United States Patent [19]
Bryant

[11] Patent Number: 5,074,853
[45] Date of Patent: Dec. 24, 1991

[54] MALE INCONTINENCE DIAPER

[76] Inventor: Tracy L. Bryant, 7285 E. Desert Palm, Tucson, Ariz. 85730

[21] Appl. No.: 533,003

[22] Filed: Jun. 4, 1990

[51] Int. Cl.⁵ .......................... A61F 5/44; A61F 13/15; A61F 13/20
[52] U.S. Cl. .................................. 604/349; 604/385.1; 604/385.2
[58] Field of Search ...................... 604/385.1, 349, 351, 604/354, 385.2, 398; 128/883, 885, 887, 888, 889, 891, 893, 894, 163, 164, 165, 402, 849, 850, 856, 857, 858, 859, 869, 874, 884; 2/69, 80

[56] References Cited

U.S. PATENT DOCUMENTS

| | | | |
|---|---|---|---|
| 2,120,465 | 6/1938 | Hartley | 128/894 |
| 2,250,840 | 7/1941 | Pomeranz | 128/402 |
| 2,658,510 | 11/1953 | Hilton | 128/165 |
| 3,858,584 | 1/1975 | Johnson | 128/286 |
| 4,033,354 | 7/1977 | De Rosa | 128/402 |
| 4,423,720 | 1/1984 | Meier et al. | 128/165 |
| 4,500,316 | 2/1985 | Damico | 604/389 |
| 4,507,121 | 3/1985 | Leung | 604/361 |
| 4,559,051 | 12/1985 | Hanson | 604/385 |
| 4,572,173 | 2/1986 | Comeau | 128/163 |
| 4,587,671 | 5/1986 | Rodriguez, Jr. et al. | 2/69 |
| 4,601,716 | 7/1986 | Smith | 604/349 |
| 4,627,846 | 12/1986 | Ternstrom | 604/349 |
| 4,675,012 | 6/1987 | Rooyakkers | 604/349 |
| 4,705,513 | 11/1987 | Sheldon et al. | 604/361 |
| 4,726,076 | 2/1988 | Douez | 2/69 |
| 4,745,634 | 5/1988 | Douez | 2/69 |
| 4,917,683 | 4/1990 | Thompson | 604/387 |
| 4,944,733 | 7/1990 | Casale | 604/385.1 |

Primary Examiner—David J. Isabella
Assistant Examiner—Elizabeth M. Burke
Attorney, Agent, or Firm—Antonio R. Durando; Harry M. Weiss

[57] ABSTRACT

A combination of improvements over prior art in order to minimize the patient's exposure to wetness, the diaper according to this invention is wrapped around the penis only, so that adjacent body parts are not in contact with the inside portion of the diaper. The garment permits a nurse to single-handedly slide it in place around the penis while the patient is either sitting or lying on his back without any need for lifting or moving him. It is also shaped to provide a compact fit for comfort and tight adherence to the body to avoid the spreading of wetness during urination.

11 Claims, 1 Drawing Sheet

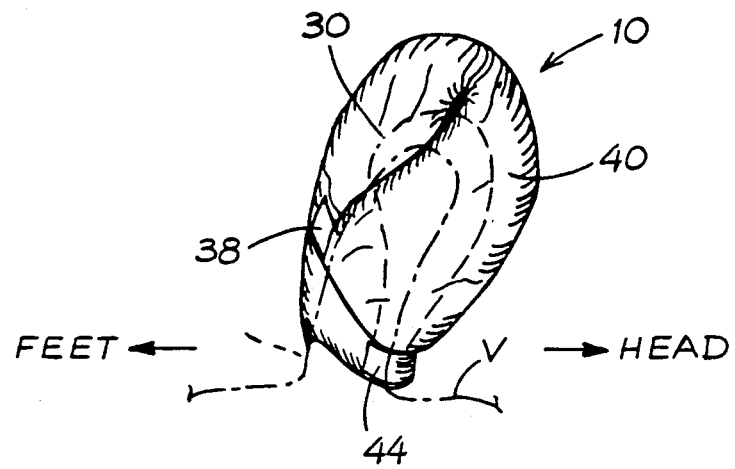
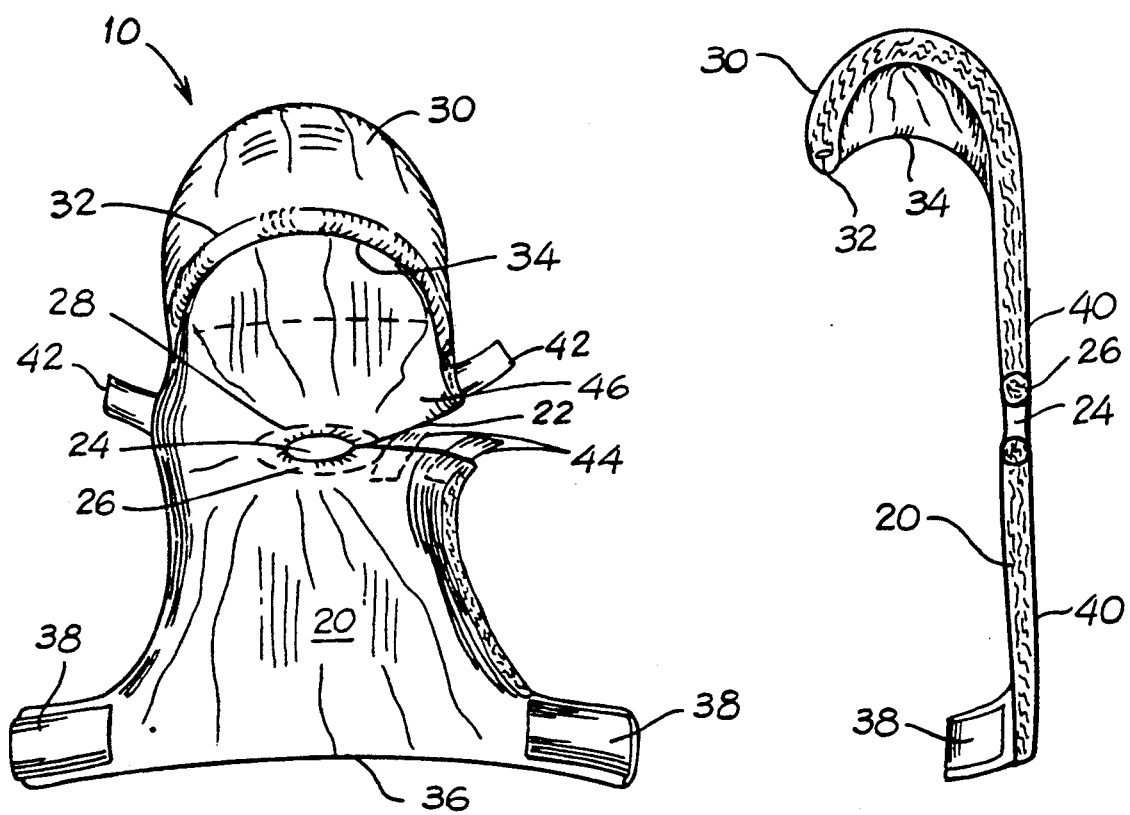

MALE INCONTINENCE DIAPER

BACKGROUND OF THE INVENTION

1. Field of the Invention

This invention to the general field of incontinence products. In particular, it provides a new and improved diaper for incontinent males who, because of disabilities, are unable to care for themselves and require assistance for their hygienic needs.

2. Description of the Prior Art

Incontinence pads, diapers and other garments have been used for many years to alleviate the practical and hygienic problems encountered by people suffering from that condition. These products vary from the traditional baby diapers in the fact that they are designed for adults, often incapacitated and bed-ridden, and therefore require greater capacity of absorption and lower propensity to cause skin irritation.

Normally, these diapers have one or more inner layers of absorbent material contained in an outer layer of waterproof fabric, so that liquid voided by the patient is retained by the diaper and prevented from leaking outside the areas of contact with his or her body. For example, U.S. Pat. No. 4,500,316 to Damico (1985) shows a diaper with a complicated support system to improve containment and avoid discharges outside the area protected by it.

Because of the contact between a patient's skin and wet material, skin irritation and rashes are a severe common problem for people who need continuous protection from incontinence discharges. In order to minimize this problem, garments have been developed with the specific purpose of rapidly absorbing the urine voided by the wearer, thus limiting its spreading to surrounding areas. This is achieved by various means of increasing the absorption capacity of the diaper in the area immediately surrounding the wearer's genitalia.

For example, U.S. Pat. No. 4,559,051 to Hanson (1985) illustrates a diaper for incontinent adults. It includes a modification specifically for males consisting of a pouch to receive and enclose the penis in order to direct the urine to a most absorbent and self-contained portion of the diaper. This prevents spreading of the wetness to other areas of the diaper and, possibly, it will help containment and prevent leaks to peripheral parts of the body as well. The purpose of the pouch is to keep the male genitalia in place during use and thus maintain direct proximity with the most absorbent portions of the diaper for optimal efficiency.

U.S. Pat. No. 3,858,584 to Johnson (1975) describes a traditional baby diaper that includes an exterior attachment for urine collection and disposal. The penis is inserted into the attachment, which is shaped like a cylindrical container, through an opening in the diaper; thus, the diaper remains dry while the urine is absorbed into the container alone. When saturated, the container can be replaced without changing the diaper. The result is that an entire new diaper need not be used unless a bowel movement has also occurred.

In U.S. Pat. No. 4,601,716 (1986), Smith describes a sanitary pouch for male use only, conceived to absorb secretions and post-urination wetness. Although intended for healthy males and not as a prosthetic for incontinence, this invention involves the idea of an absorbent and protective pocket for male adults.

In U.S. Pat. No. 4,627,846 (1986), Ternstrom shows a similar type of pouch, but for incontinent men. It is designed to slide under the scrotum and penis and enclose both to receive urine voided by the patient. The invention is directed to men whose incontinence is limited to urine, so that an entire diaper would not be necessary for protection.

Finally, U.S. Pat. No. 4,675,012 (1987) to Rooyakkers teaches a method for making yet another pouch-type absorbent diaper for incontinent males. The material is shaped to form a cup that covers the genitalia and allows air circulation to maintain skin dryness. The cup is kept in place by regular underwear against the body of the wearer.

As indicated, the incontinence diapers described in the prior art tend to cause skin irritation to the patient. In addition, they are cumbersome to use because of the difficulty involved in discretely and yet effectively handling a patient's genitalia during a diaper change.

BRIEF SUMMARY OF THE INVENTION

One objective of this invention is the development of an improved male incontinence diaper that limits the patient's exposure to wetness to the minimum extent possible in order to avoid skin irritation and rashes. This is accomplished by having a diaper wherein the material that has been wetted by urination is in contact with the patient's penis only so that the surrounding skin remains dry.

Another objective of the invention is a diaper that can be changed by a care provider discretely and with maximum comfort to the patient. For this purpose the diaper is designed with an opening whereby the patient's penis can be held while the diaper is easily wrapped around it.

A further goal of the invention is a diaper that can be changed easily and without any cooperation by the patient, who may be unable or unwilling to act in concert with the person in whose care he is entrusted. This is accomplished by a diaper that does not require lifting of the patient's pelvis during a change.

A final objective is the easy and economical manufacture of the diaper designed according to the above stated criteria. This is achieved by using commercially available components and materials, modified to fit the requirements of this invention. Various other purposes and advantages of the invention will become clear from its description in the specifications that follow and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

BRIEF DESCRIPTION OF THE DRAWINGS

FIG. 1 is a plan view of one embodiment of the diaper according to this invention, shown with the inside layer up as it lays on a flat surface.

FIG. 2 is a cross-sectional view of the diaper of FIG. 1 held vertically and illustrating the space formed by the hood portion for receiving a patient's penis.

FIG. 3 is a perspective view of the diaper of FIG. 1 as worn by a patient.

DETAILED DESCRIPTION OF THE INVENTION

This invention is based on a combination of improvements over existing diapers in order to achieve the objectives described above. To minimize the patient's exposure to wetness, the diaper is wrapped around the penis only, so that adjacent body parts are not in contact with the inside portion of the diaper. The garment is designed in such a way that permits a nurse to single-handedly slide it in place around the penis while the patient is either sitting or lying on his back without any need for lifting or moving him. It is also shaped to provide a compact fit for comfort and tight adherence to the body to avoid the spreading of wetness during urination.

Referring to FIG. 1, the preferred embodiment of a diaper 10 according to this invention is shown, as viewed from the top while it lays on a flat surface. The face 20 corresponds to the garment's inside liner that is wrapped around the patient's penis during wear. This liner is moisture permeable and absorbent, and it may consist of any material used to provide absorbency in baby diapers found in prior art, such as cotton fibers. An outside liner 40, coextensive with the bottom portion of the absorbent liner 20 (excluding the hood portion 30), consists of a moisture impermeable material made of either plastic film or impregnated fabric, such as found in the outer layer of most commercially available baby diapers. The two layers 20 and 40 are attached together by any suitable means, such as stitching or cementing of the adjacent surfaces, to form a two-layer sheet constituting the main material for the diaper. The hood portion 30 consists of a single layer of absorbent material without an impermeable back and is an integral part of layer 20. It is anticipated that additional and different kinds of layers of material may be used for particular purposes as found in the variety of diapers known in the prior art.

The diaper 10 is manufactured with a side cut 22 to allow it to slide around a penis into the opening 24, which is appropriately sized to receive and hold the penis in a comfortable but snug position. The edge of the opening 24 can be padded with additional absorbent material 26 for extra protection. Moreover, in order to improve adherence of the edge of the opening 24 to the skin of the penis, a circular elastic band 28 may be added to provide extra tightness. The elastic band should result in sufficient tension around the penis to keep it from easily sliding out of the opening 24, but not so tight as to create discomfort. Preferably, it should constrict the opening 24 to approximately ½ inch in diameter while unstretched.

The top portion of the diaper is shaped like a hood 30, formed by a semi-circular elastic strap 32, or a multiplicity of straps, pulling the outer edge 34 inward. The dimensions and shape of the diaper should be such that the hood 30 can be curled over the patient's penis, so as to provide a retaining cup, without excessive bulk that would cause discomfort. Coextensive with the inside surface of the hood 30, additional padding or absorbent material (not shown in the figures) may be added to it in order to provide extra softness and protection. Thus, once the penis is positioned in the opening 24 of the diaper, the hood 30 is folded downward to receive it and the garment's bottom portion 36 is folded upward to overlap it and form a snug enclosure surrounding the penis entirely. Tabs 38 are provided to permit the secure fastening of the lower portion 36 of the diaper after it has been folded upward to envelop the hood 30, itself being folded downward around the patient's penis. In addition, the lower part of the hood 30 and the side cut 22 may be equipped with similar tabs 42 and 44 to more efficiently fasten the hood and the two sides of the cut. All sets of tabs may simply consist of adhesive tape capable of attaching to any part of the diaper with which it is contacted, or may comprise more complicated fastening devices that include cooperating receiving components appropriately placed on the outer layer of the diaper, such as the fiber loop straps known under the "Velcro" trademark. Moreover, additional padding and absorbent material may be added around the tabs in order to improve liquid containment at the points of adherence.

This invention also describes a method of use of the diaper 10. As mentioned above, the first step consists of sliding the diaper in place around the penis of a patient who is sitting or, preferably, lying down in a supine position (as shown by the contour of the ventral area V indicated by a broken line in FIG. 3). If the patient is unable to help or uncooperative, this step can be accomplished by a care provider by holding the tip of the penis with one hand while inserting the side cut 22 of the diaper around it with the other hand. The diaper is thus placed to cause the penis to fit in the opening 24 with the impermeable layer 40 facing the body of the patient and the absorbent layer 20 facing the tip of the penis. The diaper is positioned so that the hood 30 is at the top toward the head of the patient.

The next step requires the folding of the hood 30 downwards to receive and contain the penis. By pulling and wrapping the bottom part 46 of the side cut around the hood, a pocket is formed to envelop the penis and receive any drainage into the permeable material of the liner 20. If present, tabs 42 are used to envelop the penis in the hood 30 as securely as possible. The diaper is further secured by folding its upper part 36 upwards and by wrapping it around the pocket formed according to the step above. The flaps 38 and 44 are then used to keep the various parts so folded in place. FIG. 3 illustrates the diaper so shaped as is it worn by a patient.

Upon urination, the fluid is discharged into the absorbent inner layer 20 in direct contact with the skin of the penis enveloped in the diaper and more particularly into the inside of the pocket 30, which may contain additional lining material, as described above. Because of the impermeable outer layer 40 and the snug fit of the opening 24 around the circumference of the penis, if the diaper is properly folded and fastened to form a pocket, the liquid is contained inside the diaper and the wearer's body is otherwise kept dry. This result improves the comfort level of incontinent patients who normally would have to contend with wetness all around the pelvic area. When a change becomes necessary, the diaper can be pulled off the patient without unfolding it, thus simplifying the normally unpleasant task of disposal of dirty diapers. At the same time, a new diaper can be put on the patient with minimal interference, which may be very important when dealing with bedridden individuals.

In the case of patients who are not confined to a bed or wheelchair and who, therefore, would wear the diaper while standing erect, it may be worn upside down, so as to take advantage of the hood portion of the diaper to provide a drainage cup below the penis to better collect any drainage. The use and method of application of the diaper would otherwise remain the same.

As in the prior art, the diaper of this invention can be further manufactured to include deodorant or medicinal substances in the lining to achieve specific objectives for particular applications. Similarly, the diaper could include one of a variety of wetness indicators known in the art, such as shown in U.S. Pat. No. 4,507,121 to Leung (1985) and U.S. Pat. No. 4,705,513 to Sheldon et al. (1987).

Various changes in the details, steps and materials that have been described may be made by those skilled in the art within the principles and scope of the invention herein illustrated and defined in the appended claims. Therefore, while the present invention has been shown and described herein in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent apparatuses and methods.

What I claim is:

1. A male incontinence diaper, which comprises:
   (a) a liquid absorbent cloth having a circular opening approximately at its center and having a radial cut extending from said centrally located circular opening to the outer perimeter of said cloth;
   (b) means for securing said cloth in a folded position;
   (c) a circular elastic band around said circular opening to provide stretch and tension for a snug fit around a wearer's penis; and
   (d) a hood, formed around the edge of the top end of said cloth, for receiving and holding said wearer's penis;
   said radial cut being available for sliding the diaper around said wearer's penis so as to cause it to be positioned into said hood through said circular opening and wrapped in multiple folds held in place by said securing means.

2. The male incontinence diaper described in claim 1, further comprising:
   (e) an inner liner coextensive with said hood to provide extra padding and absorbency;
   (f) a circular strip of padding and absorbent material attached to the inner edge of said circular opening for further comfort and protection to the wearer of the diaper; and
   (g) a semi-circular elastic band around the edge of said hood, provided to pull said edge inward.

3. The male incontinence diaper described in claim 2, wherein said means for securing said diaper in a folded position consists of adhesive tape strips located along the edge of said radial cut, on the bottom edge of said hood, and on the edge of the bottom end of said cloth.

4. A male incontinence diaper, which comprises:
   (a) a generally oblong cloth comprising an outer layer made of impermeable material and an opposite inner layer made of permeable and liquid absorbent lining material, said cloth having a circular opening approximately at its center and having a radial cut extending from said centrally located circular opening to the outer perimeter of said cloth;
   (b) a circular elastic band around said circular opening to provide stretch and tension for a snug fit around a wearer's penis;
   (c) a semi-circular elastic band around the edge of the top end of said cloth to form a hood of absorbent material for receiving and holding a wearer's penis;
   (d) an inner liner coextensive with said hood to provide extra padding and absorbence;
   (f) a circular strip of padding and absorbent material attached to the inner edge of said circular opening for further comfort and protection to the wearer of the diaper; and
   (b) means for securing said diaper in a folded position; said radial cut being available for sliding the diaper around a patient's penis so as to cause it to be inserted in said circular opening for wrapping it into multiple folds held in place by said securing means.

5. The male incontinence diaper described in claim 4, wherein said means for securing said diaper in a folded position consists of adhesive tape strips located along the edge of said radial cut, on the bottom edge of said hood, and on the edge of the bottom end of said cloth.

6. The male incontinence diaper described in claim 5, further comprising a wetness indicator for alerting of liquid discharges into said inner absorbent lining of the diaper.

7. A method of applying and wearing a male incontinence diaper, which comprises the following steps:
   (a) providing a generally oblong cloth comprising an outer layer made of impermeable material and an opposite inner layer made of permeable and liquid absorbent lining material, said cloth having a circular opening approximately at its center and having a radial cut extending from said centrally located circular opening to the outer perimeter of said cloth, and said cloth having means for securing it in a folded position;
   (b) sliding said cloth around a patient's penis so as to cause it to be inserted in said circular opening;
   (c) wrapping said cloth in multiple folds around the patient's penis to form a cup with the inner part constituted by said absorbent lining material and the outer part constituted by said impermeable material; and
   (d) fastening said cloth in place by said securing means.

8. The method described in claim 7, further comprising the following steps:
   (e) supplying a circular elastic band around said circular opening to provide stretch and tension and fastening the edges of said radial cut by said securing means for a snug fit around a wearer's penis; and
   (f) providing a semi-circular elastic band around the edge of the top end of said cloth to form a hood of absorbent material for receiving and holding a wearer's penis and inserting the penis into the inner portion of said hood.

9. The method described in claim 8, further comprising the following steps:
   (g) supplying an inner liner coextensive with said hood to provide extra padding and absorbence; and
   (f) supplying a circular strip of padding and absorbent material attached to the inner edge of said circular opening for further comfort and protection to the wearer of the diaper.

10. The method described in claim 9, wherein said means for securing said diaper in a folded position consists of adhesive tape strips located along the edge of said radial cut, on the bottom edge of said hood, and on the edge of the bottom end of said cloth.

11. The method described in claim 10, further comprising a wetness indicator for alerting of liquid discharges into said inner absorbent lining of the diaper.

* * * * *